United States Patent
Couderc et al.

(10) Patent No.: US 7,221,976 B2
(45) Date of Patent: May 22, 2007

(54) ANALYSIS OF THE ALTERNANS CYCLE TO CYCLE AND/OR THE VARIABILITY OF THE VENTRICULAR REPOLARIZATION WAVE IN AN ECG SIGNAL

(76) Inventors: Jean Philippe Couderc, 74 S. Main St., Pittsford, NY (US) 14534; Wojciech Zabera, 375 Warren Ave., Rochester, NY (US) 14620

(*) Notice: Subject to any disclaimer, the term of this patent is extended or adjusted under 35 U.S.C. 154(b) by 436 days.

(21) Appl. No.: 10/865,682

(22) Filed: Jun. 10, 2004

(65) Prior Publication Data

US 2005/0010124 A1    Jan. 13, 2005

(30) Foreign Application Priority Data

Jun. 10, 2003   (FR)   .................................. 03 06913

(51) Int. Cl.
*A61B 5/04*   (2006.01)
*A61N 1/37*   (2006.01)

(52) U.S. Cl. ...................... 600/515; 600/516; 607/25
(58) Field of Classification Search ................ 607/25; 600/515, 516
See application file for complete search history.

(56) References Cited

U.S. PATENT DOCUMENTS

| | | | |
|---|---|---|---|
| 5,348,020 A | | 9/1994 | Hutson ...................... 128/696 |
| 5,921,940 A | * | 7/1999 | Verrier et al. ............... 600/518 |
| 6,823,213 B1 | * | 11/2004 | Norris et al. ................. 607/9 |
| 2003/0233050 A1 | * | 12/2003 | Haghighi-Mood et al. .. 600/515 |

* cited by examiner

*Primary Examiner*—Robert E. Pezzuto
*Assistant Examiner*—Tammie K. Heller
(74) *Attorney, Agent, or Firm*—Orrick Herrington & Sutcliffe, LLP

(57) ABSTRACT

A device for the analysis of the alternans cycle to cycle and/or the variability of the ventricular repolarization wave in an ECG signal. This device extracts from an ECG signal, for each cardiac beat, a temporal segment of T samples of the ventricular repolarization wave, considered as from a moment t following a predetermined temporal origin. The T samples for B consecutive beats are aggregated and a local variance factor is evaluated. The square root of the local variance is obtained and weighted by a factor of local alternans. The device delivers at the output an index of alternans and variability $TVar_b$ function, for a given beat, local variance factor weighted by the factor of local alternans.

22 Claims, 7 Drawing Sheets

(4 of 7 Drawing Sheet(s) Filed in Color)

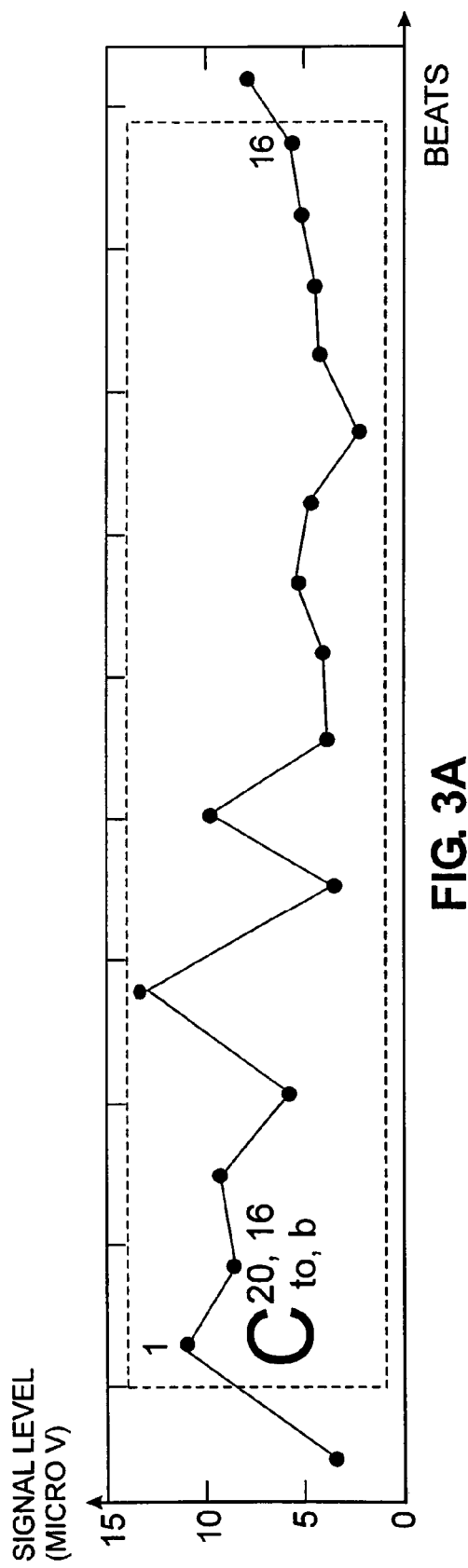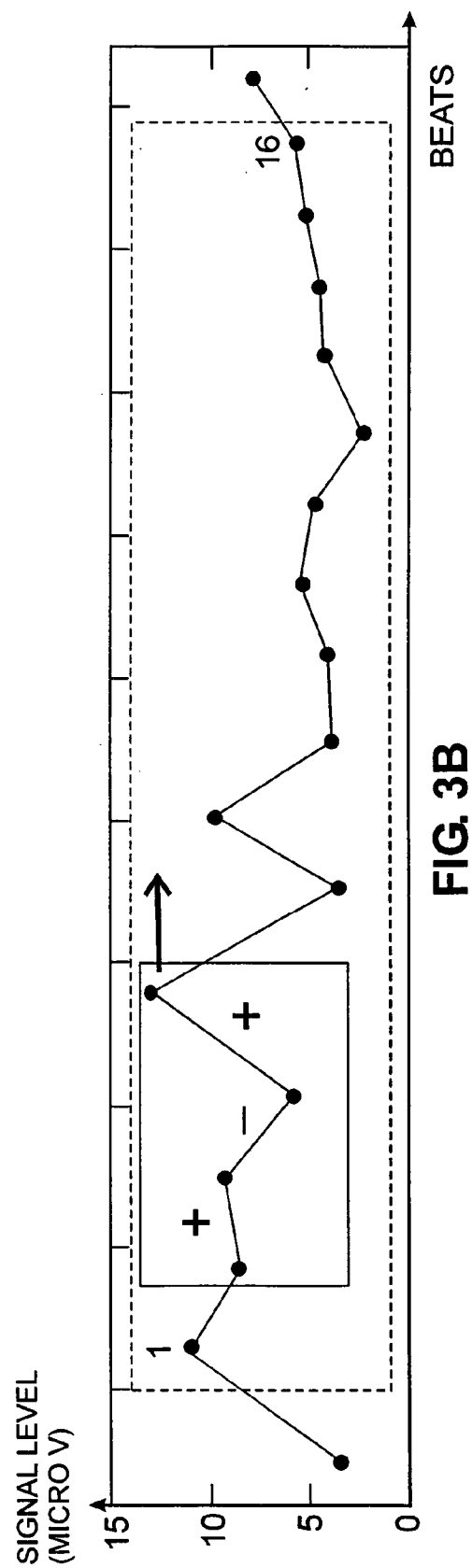

PRIOR ART FREQUENCY TECHNIQUE

A

C

PRIOR ART FREQUENCY TECHNIQUE

B

D

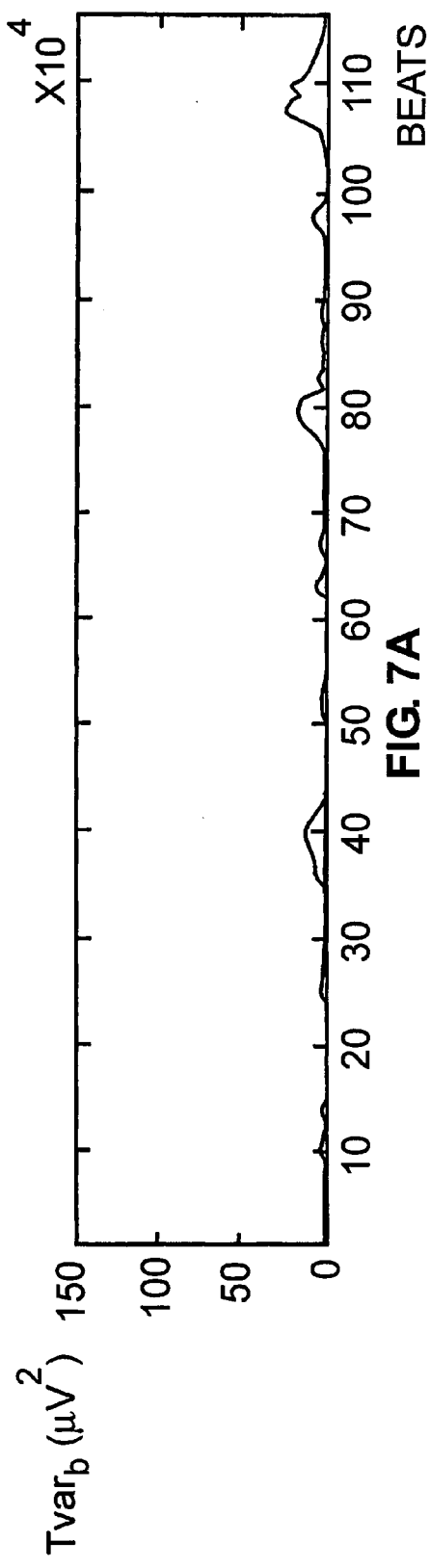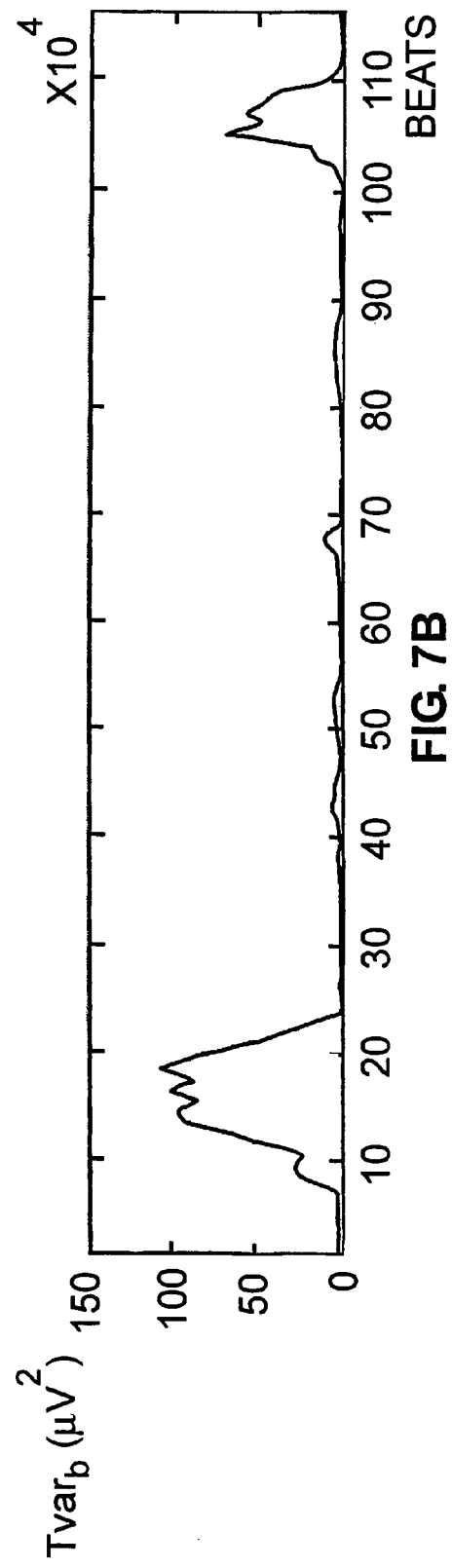
FIG. 7A
FIG. 7B

ANALYSIS OF THE ALTERNANS CYCLE TO CYCLE AND/OR THE VARIABILITY OF THE VENTRICULAR REPOLARIZATION WAVE IN AN ECG SIGNAL

FIELD OF THE INVENTION

The present invention relates to a device for the analysis of the cardiac rhythm, more particularly to the analysis of the alternans cycle to cycle and/or the variability of the ventricular repolarization wave in an ECG signal.

BACKGROUND OF THE INVENTION

An ECG signal collected (i.e. sensed or detected) by external electrodes or an endocardiac probe present in a characteristic manner a series of wave complexes known as the "PQRST" complexes corresponding to the succession of the cardiac beats of the patient. On a cycle cardiac, the QRS, complex, which represents the repolarization of the ventricles, is followed by a wave known as the "T wave" or the "repolarization wave" (these two terms will be used interchangeably hereafter). It is the electric translation on the ECG of the repolarization of the myocardic cells of the ventricles. The T wave (repolarization wave) presents an amplitude and form (shape) that are quite variable, and is very sensitive to conduction disturbances in the myocardium.

Various devices have been specifically proposed to analyze the variability of the T wave, for example, the French Patent No. Fr-A-2 784 035 (commonly assigned herewith to Ela Médical), which analyzes the T wave to diagnose the appearance and then the evolution of an ischemic state in real time, so as to be able to adapt consequently the operation of the device. In this document, the device for the analysis of the T wave is a device incorporated in an implant, e.g., a cardiac pacemaker or cardiovertor and operative in real time, by analysis of the moment of arrival of the leading edge repolarisation wave.

Another parameter of the T wave that is known to be interesting to evaluate is the alternans, which is a very small repetitive pattern of the variability, on the order of millivolts, from one beat to the following beat, in the waveform of the ECG in the temporal segment corresponding to the repolarization wave. This variation pattern is of type ABABAB . . . , i.e., if one examines every other wave, these waves are very similar, but comparing one T wave to the immediately following T wave reveals a detectable variation of the amplitude, the level of which constitutes a significant indicator of a cardiac electric instability of the patient. The presence of a T wave alternans, indicative of a non uniform repolarization of the myocardium, is in particular a very good predictor of fibrillation, and thus of the clinical risk of ventricular arrhythmia and sudden death.

In the case of a implanted defibrillator with an integrated analyzer of the T wave alternans, as described for example in French Patent No. Fr-A-2 808 213 (Medtronic Inc), it is possible to provide quickly a warning to the patient or to the doctor in the event of risk of major cardiac risk, or to even start a therapy by the device when this risk is declared.

Independently of the implanted devices integrating an analyzer functioning in real time, it also is possible to monitor for the presence of a T wave alternans based upon signals collected by a so called "Holter" recorder, i.e., an apparatus that performs an essentially uninterrupted recording of cardiac activity signals collected by means of implanted electrodes or external electrodes over a long period. The examination of the Holter recording can in this instance include the search for a possible T wave alternans, constituting an indicator of risk. Such an analysis is considerably important in identifying those patients that are likely to benefit from the implantation of an implantable defibrillator/cardiovertor as a primary preventative measure.

The presence of a T wave alternans is also a significant predictor of a degradation of the ischemic state of the patient. Indeed, an ischemic state results in an quasi-instantaneous and detectable modification of the ventricular repolarization wave (the ischemia appears following a stop or a reduction of the blood irrigation of the heart).

The search for a T wave alternans until now has been relatively difficult because the cycle to cycle variation of the alternans is very small (typically a variation of about 5 µV), in particular when compared to the mean level of the noise present in ECG signal, which noise has a typical mean level of about 10 µV. The search for a T wave alternans thus requires the implementation of means which at the same time are very sensitive and have a noise good immunity (thus implying complex algorithms and filtering).

The algorithms proposed until now have required relatively significant means for calculation (bit resolution, computation power, memory, etc.) thus implying resources for performing the calculations that do not allow for implementation in a microcomputer or more particularly in an ambulatory or implanted apparatus (unless one is willing to tolerate excessive processing times and/or lower quality in the result). However, to obtain quickly a reliable predictor of fibrillation or ischemia of the myocardium, it is significant to be able to reveal and discriminate quickly a certain number of micro-variations, which can be very significant for obtaining a reliable and relevant diagnosis.

One known technique for analyzing a T wave alternans is the spectral method (see in particular U.S. Pat. No. 4,802, 491 and Rosembaum D S et al., "Electrical Alternans and Vulnerability to Ventricular Arrhythmias," *N Engl J Med*, 1994; 330: 235–241). This technique proposes to analyze the energy variations of the frequency spectrum of ECG signal, so as to seek a peak of energy for a revealing frequency of the required fluctuation.

Another known technique for analyzing a T wave alternans is the complex demodulation technique (U.S. Pat. No. 5,842,997 and Nearing B. et al., "Dynamic Tracking of Cardiac Vulnerability by Complex Demodulation of the T-Wave," *Science*, 1991; 252: 437–440). This technique seeks to model the fluctuation of the amplitude of the T wave by a sinusoid of variable amplitude and variable phase, so as to ensure a dynamic follow-up of the variations of alternans of the T wave. Its intrinsic complexity, however, makes the method difficult to apply without addition of specific hardware circuits.

Another known technique for analyzing a T wave alternans is the temporal field analysis technique (see Verrier R. et al., "Median Beat Analysis of T-Wave Alternans to Predict Arrhythmic Death after Myocardial Infarction: Results from the Autonomic Tone and Reflexes after Myocardial Infarction Study," *Circulation*, 102, 18; 2000: II-713 (abstract)). This method concerns calculating, for alternating beats, two averages of the T wave amplitudes at a given point of the repolarization segment and quantifying the difference in amplitude between the two averages.

Another known technique for analyzing a T wave alternans is the stretching technique (see U.S. Pat. No. 5,560,638 and Berger R. et al., "Beat-to-Beat QT Interval Variability: Novel Evidence for Repolarization Ability in Ischemic and Non-Ischemic Dilated Cardiomyopathy," *Circulation* 1997;

96: 1557–1565). In this technique, one superimposes the T wave with a template and the temporal component is stretched so as to minimize the difference between the template and the analyzed beat.

Another known technique for analyzing a T wave alternans is the cross-correlation technique (see Burratini L. et al., "Computer Detection of Non-Stationary T-Wave Alternans Using New Correlative Method," *Computers in Cardiology* 1997; 42: 657–660). This technique concerns quantifying, in the temporal field, the variations of amplitude and morphology (shape) of the repolarization wave on the basis of a correlation index; each T wave is correlated with a T wave average representative of a series of beats, an alternans, positive or negative, resulting in an oscillation of the correlation index around the median value.

Another known technique for analyzing a T wave alternans is the wavelets approach (see Couderc JP et al., "Beat-to-Beat Repolarization Variability in Patient LQTS with the SCN5A Sodium Channel Gene Mutation," *PACE*, 1999, 22, 1581–1592). The ECG signal is broken up into a Gaussian sum and then processed so as to isolate the various complex components from the wave (P, QRS and T) so as to reveal singularities, and in particular an alternans for the T wave.

OBJECTS AND SUMMARY OF INVENTION

The present invention therefore proposes a new technique for the detection and quantification of the variability of the T wave in an ECG signal and more specifically an alternans of the T wave. Compared to the prior known techniques referenced above, the technique of the invention:

(1) proceeds in the temporal field as to evaluate the variability or the alternans of the repolarization wave, thus avoiding recourse to Fourier transformations or other spectral analysis techniques requiring significant means for performing calculations;

(2) does not base itself on a correlation of the signals for the synchronization and the quantification of the variability and the alternans of the T wave;

(3) allows the follow-up of an alternans or a variability of the repolarization in any ECG signal presenting a sufficient resolution in amplitude and a sufficient sampling rate, and is thus usable with any existing apparatus, on the basis of a recording carried out according to traditional and tested techniques, without requiring any dedicated apparatus or the material adaptation of the existing devices;

(4) allows to identify part of the repolarization segment where variability and/or alternans are maximum, thus increasing the relevance and the selectivity of measurement.

The device for conducting the analysis of the present invention preferably operates on a previously acquired ECG signal, collected by an implanted medical device (e.g., cardiac pacemaker having Holter functions, defibrillator or multi-site device) or an external device (e.g., ambulatory Holter recorder), that has then been filtered, sampled and digitized in a known manner.

In accordance with the present invention, the device for the analysis of the alternans cycle to cycle and/or variability of the ventricular repolarization wave in ECG signal includes:

means for extracting from the ECG signal, for each cardiac beat, a temporal segment of T samples of the ventricular repolarisation wave, considered from a moment t according to a predetermined temporal origin;

means for memorizing the extracted T samples for B consecutive beats, considered starting from the $b^{th}$ beat of ECG signal, so as to select and memorize a two-dimensional aggregate of T×B contiguous samples of signal in the "time-beats" space;

means for calculating a factor corresponding to a local variance of the ventricular repolarisation wave, representative of a measurement of the variance of the signal level in the samples inside the aggregate; and weighting means for:
  detecting and counting an alternans cycle to cycle of the ventricular repolarization wave on B beats of the aggregate,
  weighting the factor of local variance by a local alternans factor varying between a minimum and a maximum, the minimum corresponding to a complete absence of detection of an alternans over the beats of the aggregate, and the maximum corresponding to a detection of a permanent and recurring alternans over all the beats of the aggregate, and
  delivering an index of the alternans and variability function, for a given beat, wherein the factor of the local variance is weighted by the factor of local alternans.

According to various advantageous embodiments, the weighting by the factor of local alternans is operated on the square root of the factor of local variance. In an alternate preferred embodint, the weighting means is also able to calculate the factor of local alternans for a predetermined plurality of temporal sub-segments of different durations and different origins within the aggregate, then to select among these sub-segments the one for which the corresponding factor of local alternans is a maximum, so as to weight the factor of local variance corresponding to the maximum local alternans factor of sub-segment thus selected.

In yet another embodiment, the weighting means are able to calculate the factor of local alternans by performing a study and quantification of the repetition of a preset pattern of alternans within the aggregate, for the same position of the sample in the temporal segment. This calculation can in particular be operated by research and counting of the consecutive changes of sign of the derivative of the signal in the field of the beats, for the same position of the sample in the temporal segment.

Preferably, the device also includes means for pre-treating the signal before its application to the extracting means, such that the means for pre-treating includes at least one device selected from among the group including: a low-pass filter; a low-pass filter with limited impulse response; a filter for the elimination of the isoelectric line; and a filter for the elimination of the respiratory component. More than one such device could be used.

Further, the device also preferably includes means for identifying in the ECG signal a sequence of beats presenting, for the duration of B consecutive beats, a stable heartbeat rate and comprising only cycles of sinusal origin, excluding the stimulated cycles generated by a cardiac pacemaker, and to apply to the extracting means only that sequence of samples. The means for selecting can in particular calculate RR intervals of the aforesaid B consecutive beats, and define a stable heartbeat rate for this sequence of samples if none of the RR intervals varies by more than a given percentage, in particular not more than 10%, compared to the average RR interval value calculated over B beats.

BRIEF DESCRIPTION OF THE DRAWINGS

The patent or application file contains at least one drawing executed in color. Copies of this patent or patent application publication with color drawing(s) will be provided by the U.S. Patent and Trademark office upon request and payment of the necessary fee.

Further benefits, features and characteristics of the present invention will become apparent to a person of ordinary skill in the art in view of the following detailed description of preferred embodiments of the present invention, made with reference to the annexed drawings, in which:

FIGS. 3a and 3b illustrate the manner of calculating the factor of local variance and the factor of local alternans for the aggregate isolated from FIG. 2;

FIGS. 7a and 7b show the variation over the course of time of the index of variability and of alternans in the case of a follow-up in real time, respectively, for a healthy subject and a patient with alternans of the T wave.

DETAILED DESCRIPTION OF THE INVENTION

Figure 1:
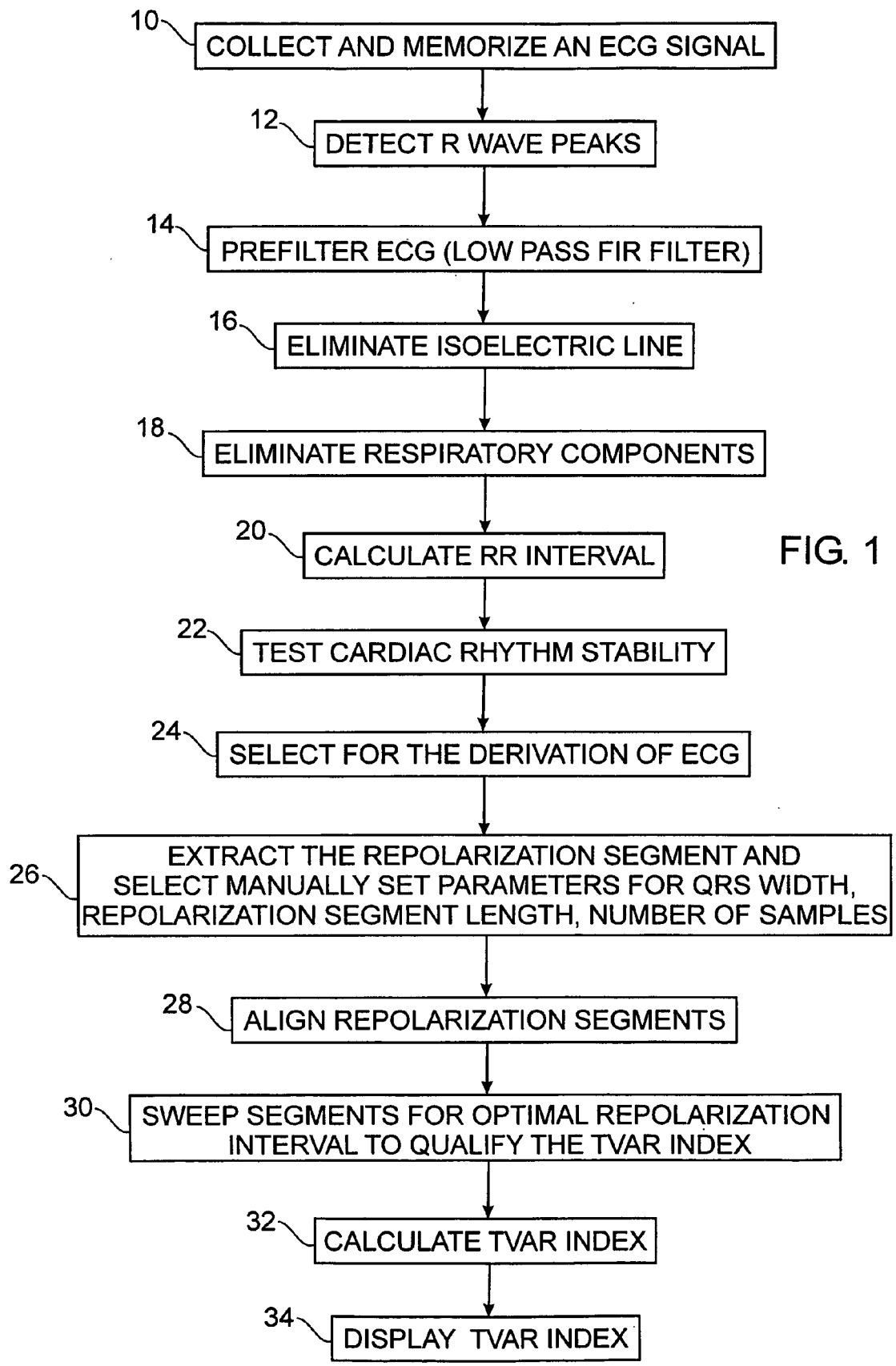
FIG. 1 is a flow diagram showing the successive steps for the treatment of the signal leading to a determination of an index of variability and of alternans.

FIG. 1 illustrates the various steps of treatment of the signal. First of all (step 10), an ECG signal is collected and memorized in digital form as a succession of samples of variable amplitude. As indicated above, the ECG signal may be previously collected by an implanted medical device (cardiac pacemaker having Holter functions, defibrillator or multi-sites device) or by an external device (ambulatory Holter recorder), then filtered, sampled and digitized in any conventional a way in itself known.

The following step (step 12) involves detecting the peaks of the wave R in the ECG signal, so as to individualize the successive beats constituting the ECG signal.

The signal is then preferably subjected to a pre-filtering (step 14), advantageously a low-pass filtering by an FIR filter (i.e., a filter with limited impulse response, which is a non-recursive digital filter).

The continuous component corresponding to the isoelectric line is then eliminated (step 16), as well as the respiratory components, which result in slow variations of the average level of the signal (step 18).

The device then calculates the value of the RR interval over a series of successive beats (step 20), so as to continue the analysis of the repolarization segment only under conditions of a stable cardiac rhythm. The stability, for example, is defined by an RR interval variation lower than 10% (step 22).

In the case of a surface ECG, the device then selects one of the known derivations (step 24), for example, derivation VM, A, B or C for a device with 4 channels. Other devices (typically to 2, 3, 5, 9 or 12 channels) can be used, the selection relating then to one of channel 1 to 12, or A to L.

For each beat, the device then functions to extract the segment of repolarization on which the analysis will be specifically carried out. A certain number of parameters can be manually selected for this purpose, in particular: (i) the width of the QRS; (ii) the length of the repolarisation segment; and (iii) the number of samples of the signal considered for the T wave division, an essential parameter for the identification of the portion of the T wave in which alternans and/or variability are maximum (step 26).

The repolarization segments thus individualized are then aligned, side by side, in a manner explained in more detail below within reference to FIG. 2 (step 28). The data thus gathered are swept so as to seek the optimal interval of the repolarization segment for the quantification of the index of variability and of the alternans of the T wave (step 30). This index then is calculated (step 32) in a manner described below, and then displayed (step 34), for example, in the manner shown on the FIGS. 4a and 4b.

The technique of the invention thus aims at extracting from the ECG signal an index representative of the variability of the T wave, or more particularly of the alternans and the variability of the T wave, an index that is referenced as "index TVar".

Primarily, the method implemented by the device of the invention consists in carrying out a two-dimensional analysis, at the same time, in the temporal field and the field of the successive beats (herein the "time/beats" space). The use of the temporal field for the study of the variability and the alternans of the T wave has the advantage of a good compromise between the temporal resolutions and the digitized signal amplitude, as well as, as it will be seen below, the possibility of identifying and of isolating the most significant part of the T wave for the quantification of the variability and the alternans. The use of the field of the beats makes it possible to better identify transitory phenomena of variability and alternans in the case of non sinusal beats, for example, for short periods of exercise during the daily activity of the carrier of a Holter recording.

Figure 2:
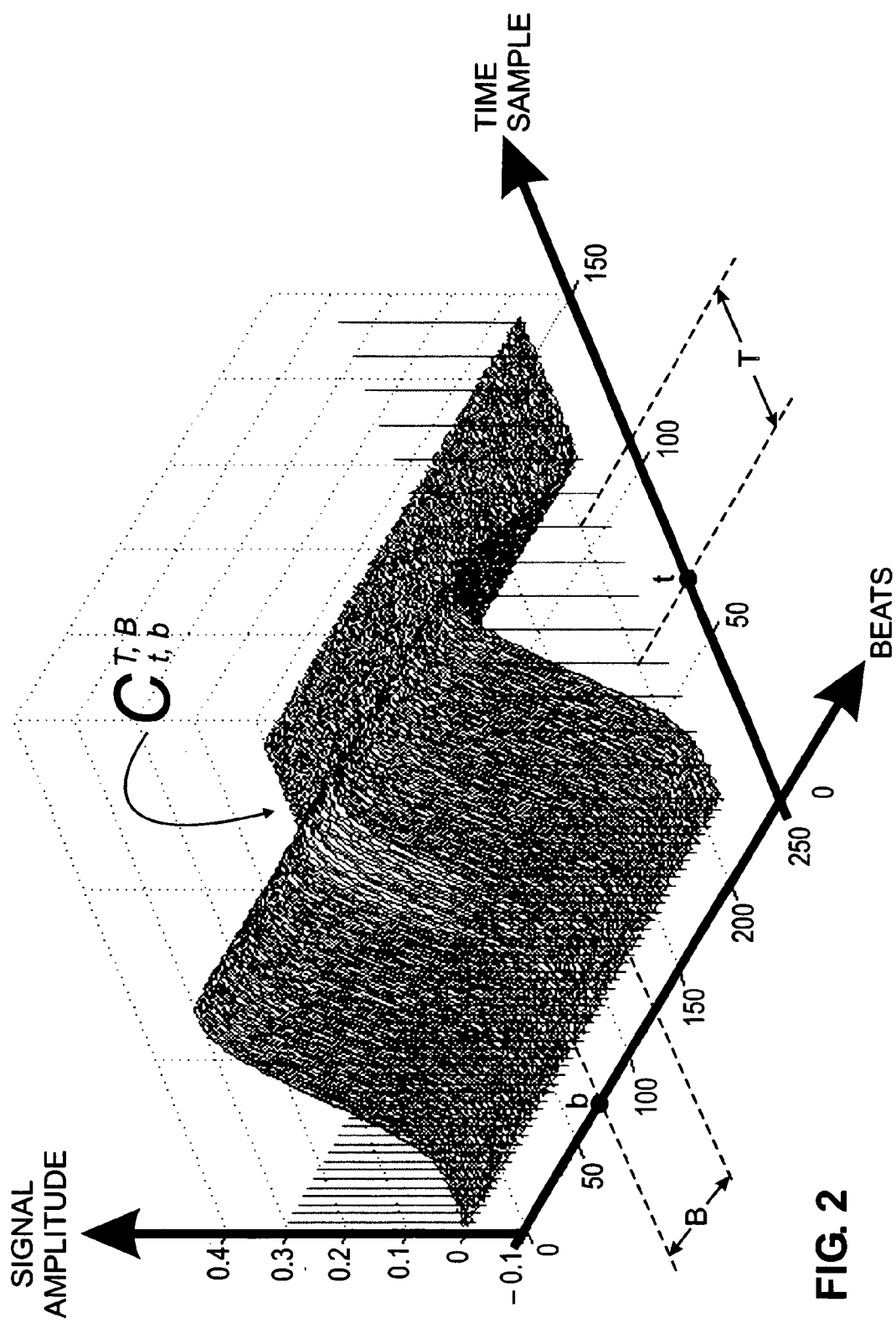
FIG. 2 is a representation in a three-dimensional space of the successive cardiac cycles, making it possible to reveal a local aggregate from which the index of alternans and variability may be calculated.

FIG. 2 is a three-dimensional representation of the respective T-waves of the successive beats of ECG signal, these T-waves having been isolated for each beat and juxtaposed so as to give a representation showing the evolution of successive beats. The representation of FIG. 2 is as follows. In the X-coordinate: the time, counted in a number of samples starting from an origin corresponding to a moment of arrival of the repolarization wave, given in a identical way from one beat to the next (the moment of arrival of the repolarization wave can be, for example, given in the way described in the above mentioned FR-A-2 784 035). The ordinate (Y axis) is beats, counted in a number of beats since a given origin from which one detected an uninterrupted succession of beats presenting a stable heartbeat rate (interval RR). On the side (a "Z" axis): the level of the signal, in microvolts (digitized values).

The first step consists in isolating, in the two-dimensional space time-beats, an aggregate of samples, designated $C_{t,b}^{T,B}$, made up of B×T samples: located on a segment length T and temporal origin t of each repolarization wave, and this for B successive beats, counted starting from the $b^{th}$ beat.

One can thus, for example, isolate an aggregate $C_{t,b}^{20,16}$ for the same segment from T=20 samples, considered on B=16 successive beats.

Starting from this aggregate of samples, the device of the invention will calculate an index, designated $TVar_b$, giving a measurement of the variability of the T wave in a temporal position t of this wave, this measurement being weighted by a factor representative of the occurrence, more or less recurring, of an alternans. In other words, the index $TVar_b$ is a measurement of a combination of the variability of the T wave and alternans of the T wave. This index $TVar_b$ can be expressed in the form:

$$TVar_b = \sqrt{Var(C_{t,b}^{Tm,B})} \times Max_{Tm,to}(W(C_{t,b}^{T,B}))$$

The first term $\sqrt{Var(C_{t,b}^{Tm,B})}$ of this expression is the square root of the local variance, which function gives a measurement of the variability of the signal within the aggregate in the area where alternans is maximum (the manner in which one determines this area of maximum alternans is discussed below).

The second term of the expression includes a factor $W(C_{t,b}^{T,B})$ of a local alternans whose value varies from 0 to 1 ($0 \leq W(C_{t,b}^{T,B}) \leq 1$) with $W(C_{t,b}^{T,B})=1$ in the event of permanent, perfectly recurring alternans over the totality of B beats of the aggregate and, conversely, $W(C_{t,b}^{T,B})=0$ in case of the total absence of alternans over these B beats.

The factor of local alternans $W(C_{t,b}^{T,B})$ is calculated for various lengths T of the repolarization sector and for various temporal origins t on the same segment, i.e., in other words, for an aggregate $C_{t,b}^{T,B}$ where a sweeping algorithm varies the parameters t and T within previously fixed, for example, by a manual parameter setting.

This search for a maximum will give values Tm and to, thus corresponding, respectively, to the length and the temporal origin of the repolarization segment for which the factor of local alternans, i.e., $C_{to,b}^{Tm,B}$, is maximum.

The local variance $Var(C_{t,b}^{Tm,B})$ is evaluated for the aggregate thus isolated.

The corresponding factor of local alternans $W(C_{t,b}^{T,B})$ is applied as a weighting factor, thus giving for each beat B an index of variability and alternans $TVar_b$:

$$TVar_b = \sqrt{Var(C_{t,b}^{Tm,B})} \times Max_{Tm,to}(W(C_{t,b}^{T,B}))$$

One now will indicate more specifically, with reference to FIGS. 3a and 3b, the manner in which one calculates the local variance factor $Var(C_{t,b}^{Tm,B})$ and the local alternans factor $W(C_{t,b}^{T,B})$ The local variance $Var(C_{t,b}^{Tm,B})$ is obtained by a traditional calculation of variance, that is to say:

$$Var(C_{to,b}^{Tm,B}) = \frac{1}{B}\left(\sum_{n=b}^{b+B-1} \left(S_{t_0}^{Tm}(n) - \overline{S_{t_o}^{Tm}}\right)^2\right),$$

with:

$$S_{t_0}^{Tm}(n) = \frac{1}{Tm}\sum_{k=to}^{to+Tm-1} S_k(n), \text{ and}$$

$$\overline{S_{t_o}^{Tm}} = \frac{1}{B}\sum_{k=b}^{b+B-1} S_{t_o}^{Tm}(k),$$

T=Tm representing the optimal duration ensuring the highest value of the weight function (local alternans), $S_k(n)$ being the amplitude of the repolarization segment for beat N and the sample k, $S_{t_o}^{Tm}(n)$ being the average amplitude of the repolarization in the aggregate located at the sample to and including Tm samples, for a given n beat, and $\overline{S_{t_o}^{Tm}}$ being the average amplitude of $S_{t_o}^{Tm}(n)$ on B beats included in the aggregate.

Thus, for example, on the basis of aggregate of B×Tm samples starting for example at the moment t=20 starting from b=16th beat:

$$Var(C_{to,b}^{20,16}) = \frac{1}{B}\left(\sum_{n=b}^{b+15} \left(S_{t_0}^{20}(n) - \overline{S_{t_o}^{20}}\right)^2\right),$$

i.e., the variance of the 20th sample of the T wave, considered on a sliding window (represented in dash on FIG. 3a) of 16 successive beats.

One now will indicate more specifically, with reference to FIG. 3b, the way in which the factor of local alternans $W(C_{t,b}^{T,B})$ is calculated.

The device seeks, on the successive beats, the smallest elementary pattern for alternans, i.e., as indicated within the framework in full line on the FIG. 3b, a pattern of four successive beats presenting three inversions of sign, of type "+−+: or −+−". In the illustrated example, the pattern is of the type "+−+", i.e., from one beat to the following, the level increases, then decreases, then increases again.

Once the number of beats of the aggregate are fixed, the device examines the cycle to cycle variance of the signal level in order to determine the occurrence (presence of a pattern "+−+" or "−+−"), or not, of a pattern of alternans and determines the proportion, between 0 and 100% (factor $W(C_{t,b}^{T,B})$) of the occurrence of this pattern on the series of beats.

More precisely, this factor $W(C_{t,b}^{T,B})$ can be numerically given in the form:

$$W(C_{t,b}^{T,B}) = \frac{1}{(b-k)}\sum_{n=B}^{B+b-k-1} ALT_n.$$

The function $ALT_n$ is a function ensuring the counting of the number of basic patterns for alternans inside a given aggregate, with:

$$ALT_n = \frac{1}{2(k-1)}\sum_{l=n}^{n+k-2}\left|\frac{d}{db}\left(\text{sign}\left(\frac{d(S_l - \min(S))}{db}\right)\right)\right|.$$

Thus, $ALT_n$ equals 1 if all the beats following the beat n present an alternans.

The weight function (factor of local alternans) $W(C_{t,b}^{T,B})$ for a given $C_{t,b}^{T,B}$ aggregate is represented by the average value of the occurrence of the basic alternans pattern inside this aggregate.

Figure 4A:
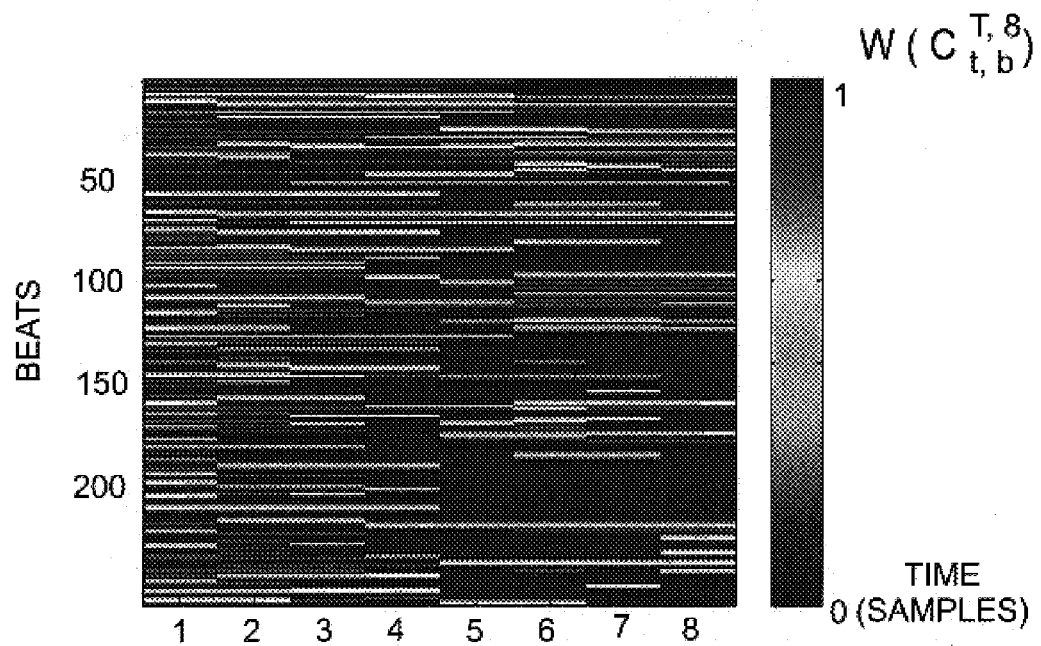
FIGS. 4a and 4b illustrate displays of the variations of the index of variability of alternans, respectively, for a patient with documented alternans of the T wave and for a healthy subject.
Figure 4B:
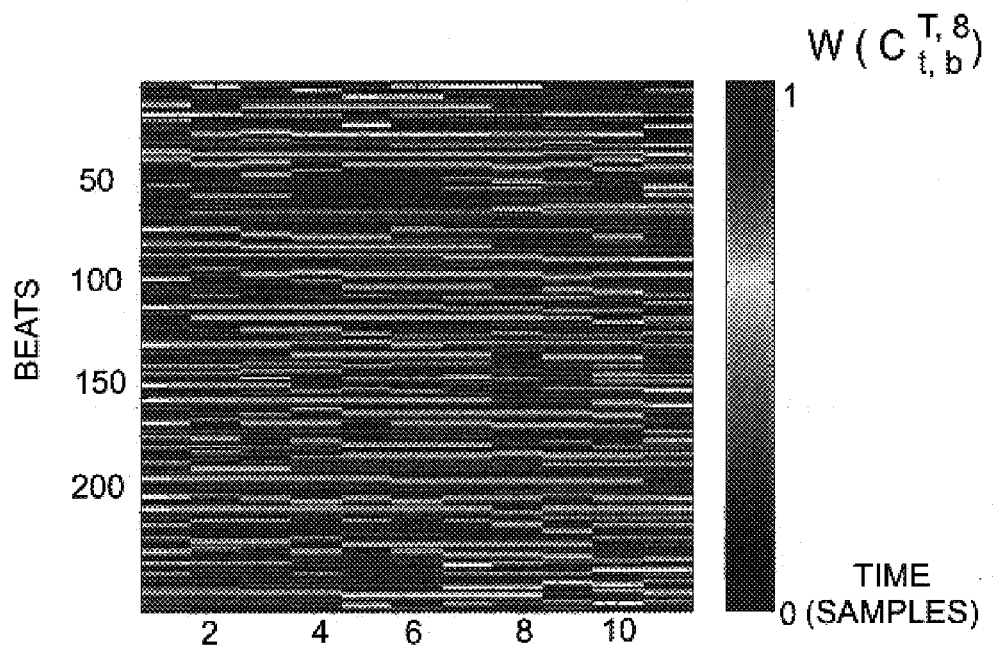

One now will give, with reference to FIGS. 4a and 4b, examples showing the way in which these parameters can vary in the time/beat space, respectively for a patient presenting a proven alternans of the T wave (FIG. 4a), and for a patient not presenting this symptom (FIG. 4b).

The FIG. 4a and the FIG. 4b show the distribution of the values of the weighting factor $W(C_{t,b}^{T,B})$ with:

In X-coordinate: the temporal position of the aggregate inside the T wave (for example, the aggregate n° 1 corresponds to the first 40 ms of the T wave, the aggregate n° 2 lies between 40 and 80 ms inside the T wave, etc.), In Y-ordinate: the succession of the beats, and on the Z axis side: the amplitude, between 0 and 1, of the factor of alternans (weighting factor $W(C_{t,b}^{T,B})$), on the basis of a gray scale (false colours).

One sees very clearly, in the patient presenting a documented alternans of T wave, coefficients $W(C_{t,b}^{T,B})$ significantly high revealing an alternans located in the last aggregates of the segment (center and right part of FIG. 4a). On the contrary, for a patient without alternans, the values of $W(C_{t,b}^{T,B})$ are dispersed over much of the segment and the weighting by the local alternans is as a whole much lower (FIG. 4b).

Figure 5A:
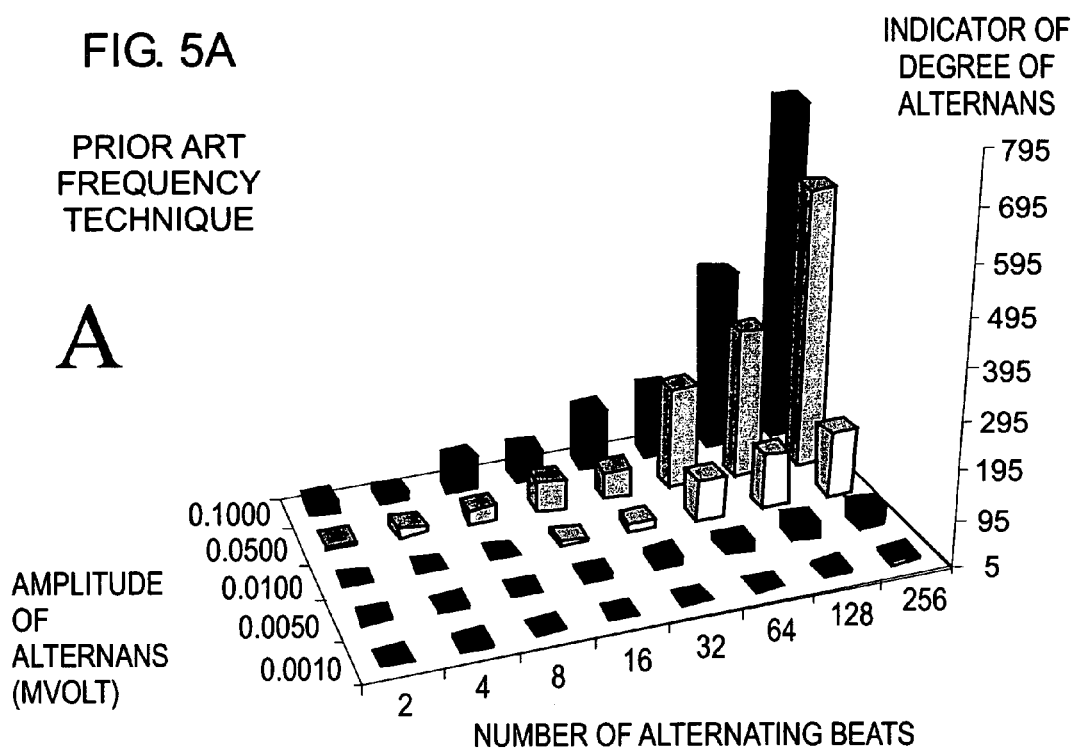
FIGS. 5a and 5b are histograms illustrating the respective performances of the analysis in terms of sensitivity for a prior art frequency technique and the technique of the present invention.
Figure 5B:
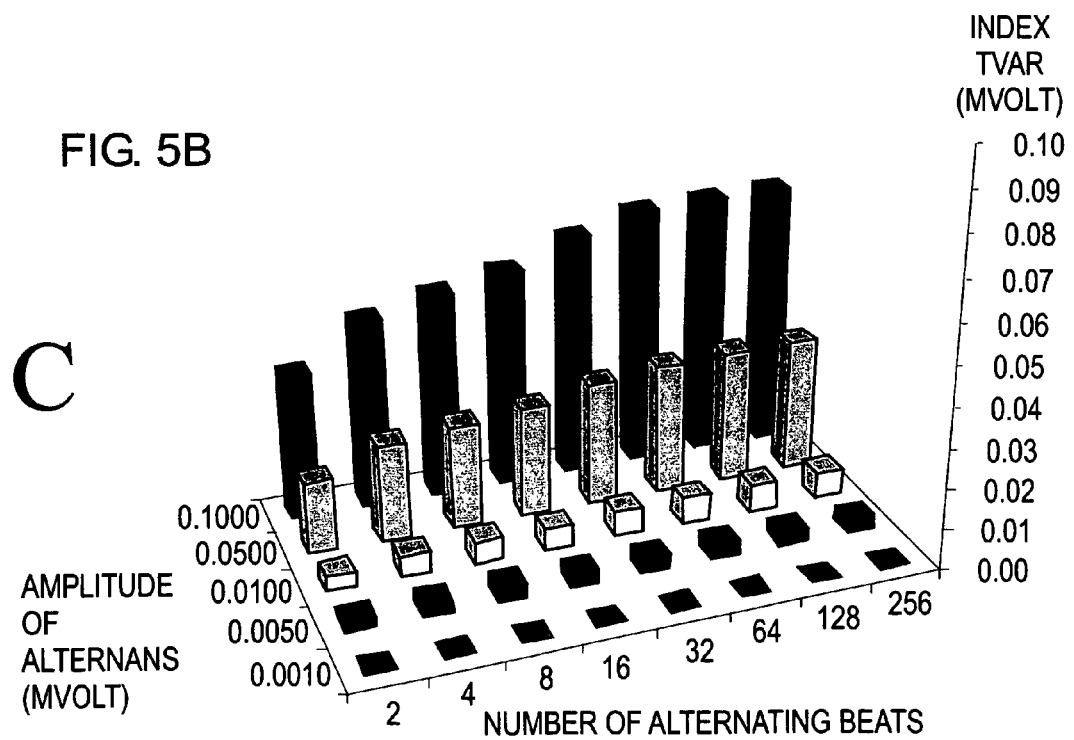
Figure 6A:
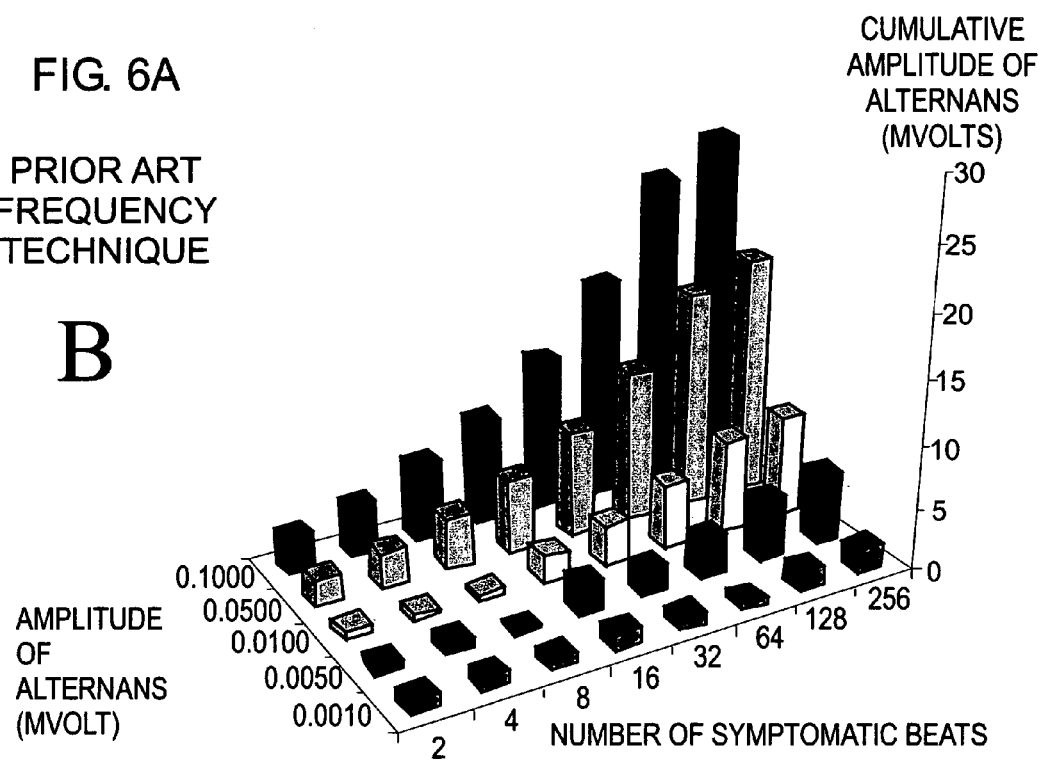
FIGS. 6a and 6b are histograms illustrating the respective performances of the analysis in terms of specificity, for a prior art frequency technique and the technique of the present invention.
Figure 6B:
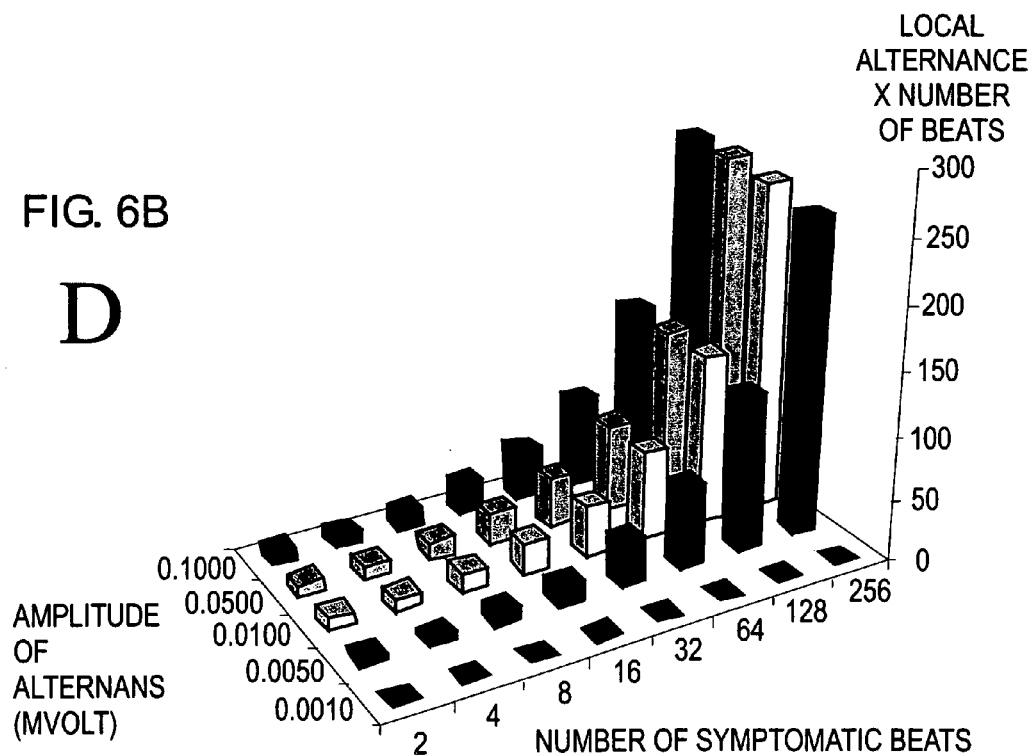

FIGS. 5a, 5b, 6a and 6b are three-dimensional column charts carried out on the basis of simulation, respectively for a traditional frequency technique (FIGS. 5a and 6a) and by the technique implemented by the device of the invention (FIGS. 5b and 6b). These figures are histograms giving the values of various parameters for a simulated signal with, in X-coordinate, an increasing number of beats presenting an alternans and, in the Y-ordinate, an increasing amplitude of this alternans cycle-to-cycle.

The illustrated parameters are as follows: FIG. 5a (prior art frequency technique): rate of alternans, giving a statistical estimate of the level of alternans in the signal; FIG. 5b (technique of the invention): estimate of the level of alternans starting from the index TVar; FIG. 6a (prior art frequency technique): voltage value of cumulated alternans, giving an estimate of alternans cumulatively on the totality of the signal; and FIG. 6b (technique of the invention): number of beats presenting an alternans, obtained by the product of the factor of local alternans $W(C_{t,b}^{T,B})$ with the number of beats of the signal.

The comparison of FIGS. 5a and 5b show in particular a sensitivity notably higher when it is a question of detecting alternans of low amplitude. These figures also show the superiority of the technique of the invention, compared to the prior art technique, to detect the occurrence of alternans only present on a low number of beats.

FIGS. 6a and 6b confirm the preceding observations, this time with regard to the evaluation of the number of symptomatic beats (by the technique of the invention) and of the estimate of the voltage value of alternans (by the prior art frequency technique). Here still, except for alternans of very low amplitude, one notes that the technique of the invention allows for a better estimate of the number of symptomatic beats when only a low number of beats presents an alternans.

FIGS. 7a and 7b illustrate representing clinical results obtained, respectively on a healthy subject (FIG. 7a) and on a patient presenting of the episodes of alternans of the T wave (FIG. 7b), when the technique of the invention is used for an uninterrupted follow-up of the index of variability and alternans TVar. These figures illustrate the evolution of the parameter $TVar_b$ to the current of the successive beats (identified by their temporal position b in the sequence of beats that are the subject of the patient follow-up).

The technique of the invention makes it possible to detect even short episodes of alternans of the T wave (in the illustrated example, a duration of from 10 to 15 beats), which makes it possible to practically ensure a follow-up of this parameter in real time. It becomes thus possible to study the frequency of appearance of a sporadic alternans, its average duration, to correlate it with other indicators (effort, activity, etc.) so as to be able to provide to the clinician relevant information for a possible diagnosis of risk of fibrillation and/or myocardial ischaemia. It will be noted that the technique of the invention does not produce false positive results, the level of the index $TVar_b$ remaining always quasi-null over the course of time in a healthy patient (FIG. 7a).

Suitable devices for which the present invention has application include, for example, for active implantable medical devices such as the Symphony, Rhapsody, and Alto brand devices, with or without multi-site pacing capabilities, all available from Ela Medical S. A., Montrouge, France. For external ambulatory devices, suitable devices are the Spiderflash and Spiderview model devices, and other Holter recording devices, also available from Ela Medical. These devices are microprocessor based systems with memory, data registers and the like (microcontrollers) having circuits for receiving, conditioning and processing detected electrical signals collected by implantable devices such as ECG signals. Suitable software routines to implement the aforementioned functions in accordance with the present invention are believed to be within the abilities of a person of ordinary skill of the art.

One skilled in the art will appreciate that the present invention can be practiced by other than the described embodiments, which are presented for purposes of illustration and not of limitation.

We claim:

1. A device for the analysis of the cycle to cycle alternans and/or the variability of the ventricular repolarisation wave in an ECG signal which includes a series of cardiac beats each beat having a ventricular repolarization wave for assessing cardiac instability, comprising:

means for extracting from an ECG signal, for each cardiac beat, a temporal segment of T samples of the ventricular repolarisation wave, considered as from a moment t following a predetermined temporal origin;

means for memorizing said extracted T samples for B consecutive beats considered starting from the b beat of ECG signal, so as to select and memorize a two-dimensional aggregate of T×B contiguous samples of signal in time-beats space;

means for calculating a local variance factor of the ventricular repolarisation wave, representative of a measurement of the variance of the signal level of the samples inside said aggregate; and weighting means operable:

to detect and count alternans cycle to cycle of the ventricular repolarization wave on B beats of the aggregate, to weight the local variance factor by a factor of local alternans variable between a minimum, corresponding to a complete absence of detection of alternans on the beats of the aggregate, and a maximum, corresponding to a detection of a permanent and recurring alternans on all the beats of the aggregate, and to deliver at the output an index of alternans and variability function wherein for a given beat, said local variance factor is weighted by the factor of local alternans.

2. The device of claim 1, wherein said factor of local alternans further compromises a factor comprising a square root of the local variance factor.

3. The device of claim 1, in wherein said weighting means further comprises:
   means for calculating the factor of local alternans for a predetermined plurality of temporal sub-segments of different durations and different origins within said aggregate;
   means for selecting among said sub-segments a sub-segment for which the corresponding factor of local alternans is a maximum; and
   means for weighting said local variance factor corresponding to the selected sub-segment by said maximum factor of local alternans.

4. The device of claim 3, wherein said factor of local alternans further compromises a factor comprising a square root of the local variance factor.

5. The device of claim 1, wherein said weighting means further comprises means for calculating said factor of local alternans based upon a research and quantification of the repetition of a preset alternans pattern inside the aggregate, for the same position of the sample in the temporal segment.

6. The device of claim 5 wherein said weighting means further comprises means for calculating the factor of local alternans based upon a research and counting of the consecutive changes of sign of derivative from the signal in the field of the beats, for the same position of the sample in the temporal segment.

7. The device of claim 1, further comprising means for pre-treating the signal before its application to said extracting means, said pretreatment means including at least one of the group including: a low-pass filter; a low-pass filter impulse response filter; a filter for the elimination of the isoelectric line; and a filter for the elimination of the respiratory component.

8. The device of claim 1, further comprising means for selecting samples in the ECG signal corresponding to a sequence of beats presenting, over all the duration of B consecutive beats, a stable cardiac rhythm, said stable cardiac rhythm comprising only cycles of sinusal origin and not the cycles generated by a cardiac stimulation, and means for applying to said means for extracting only one such sequence of selected samples.

9. The device of claim 8, wherein said selecting means further comprises means for calculating RR intervals of B consecutive beats, and means for defining a stable cardiac rhythm for said sequence of selected samples if none of said RR intervals varies by more than a first percentage.

10. The device of claim 9 wherein said first percentage further comprises not more than 10% compared to the average value of RR interval calculated on B beats.

11. The device of claim 1 wherein the ECG signal further comprises a recorded ECG waveform comprising a plurality of cardiac events, said ECG sign having been filtered, sampled and digitized.

12. A process for the analysis of the cycle to cycle alternans of the variability of the ventricular repolarisation wave in an ECG signal which includes a series of cardiac beats each beat having a ventricular repolarization wave for assessing cardiac instability, comprising:
   extracting from an ECG signal, for each cardiac beat, a temporal segment of T samples of the ventricular repolarisation wave, considered as from a moment t following a predetermined temporal origin;
   memorizing said extracted T samples for B consecutive beats considered starting from the b beat of ECG signal, so as to select and memorize a two-dimensional aggregate of T×B contiguous samples of signal in time-beats space;
   calculating a local variance factor of the ventricular repolarisation wave, representative of a measurement of the variance of the signal level of the samples inside said aggregate; and
   detecting and counting alternans cycle to cycle of the ventricular repolarization wave on B beats of the aggregate,
   weighting the local variance factor by a factor of local alternans variable between a minimum, corresponding to a complete absence of detection of alternans on the beats of the aggregate, and a maximum, corresponding to a detection of a permanent and recurring alternans on all the beats of the aggregate, and
   delivering at an output an index of alternans and variability function wherein for a given beat, said local variance factor is weighted by the factor of local alternans.

13. The process of claim 12, further comprising providing said factor of local alternans based upon a square root of the local variance factor.

14. The process of claim 12, further comprising:
   calculating the factor of local alternans for a predetermined plurality of temporal sub-segments of different durations and different origins within said aggregate, and
   selecting among said sub-segments a sub-segment for which the corresponding factor of local alternans is a maximum, and
   weighting said local variance factor corresponding to the selected sub-segment by said maximum factor of local alternans.

15. The process of claim 14, further comprising providing said factor of local alternans based upon a square root of the local variance factor.

16. The process of claim 12, further comprising calculating said factor of local alternans based upon a research and quantification of the repetition of a preset alternans pattern inside the aggregate, for the same position of the sample in the temporal segment.

17. The process of claim 16 further comprising calculating the factor of local alternans based upon a research and counting of the consecutive changes of sign of derivative from the signal in the field of the beats, for the same position of the sample in the temporal segment.

18. The process of claim 12, further comprising pre-treating the signal before said extracting step, wherein said pre-treating is selected from among at least one of the group consisting of low-pass filtering; low-pass filtering with an impulse response filter; identifying and eliminating an isoelectric line; and identifying and eliminating a respiratory component.

19. The process of claim 12, further comprising selecting samples in the ECG signal corresponding to a sequence of beats presenting, over all the duration of B consecutive beats, a stable cardiac rhythm, said stable cardiac rhythm comprising only cycles of sinusal origin and not the cycles generated by a cardiac stimulation, wherein said extracting step further comprising extracting only one such sequence of selected samples.

20. The process of claim 19, wherein selecting said one sequence further comprises calculating RR intervals of B consecutive beats, and defining a stable cardiac rhythm for said sequence of selected samples if none of said RR intervals varies by more than a first percentage.

21. The process of claim 19 wherein selecting said one sequence further comprises calculating RR intervals of B consecutive beats, and defining a stable cardiac rhythm for said sequence of selected samples if none of said RR intervals varies by more not more than 10% compared to the average value of RR interval calculated on B beats.

22. The process of claim 12 wherein the ECG signal further comprises a recorded ECG waveform comprising a plurality of cardiac events, said ECG sign having been filtered, sampled and digitized.

* * * * *